(12) United States Patent
Minnucci et al.

(10) Patent No.: US 10,982,270 B2
(45) Date of Patent: Apr. 20, 2021

(54) METHOD OF FLUORESCENT DETECTION OF ISOTHERMAL LOOP-MEDIATED AMPLIFICATION (LAMP) OF A TARGET NUCLEIC ACID, OLIGONUCLEOTIDES AND KITS THEREOF

(71) Applicant: DIASORIN S.p.A., Saluggia (IT)

(72) Inventors: Giulia Minnucci, Settimo Milanese (IT); Riccardo Mesturini, Rho (IT)

(73) Assignee: DiaSorin S.p.A., Saluggia (IT)

( * ) Notice: Subject to any disclaimer, the term of this patent is extended or adjusted under 35 U.S.C. 154(b) by 119 days.

(21) Appl. No.: 16/061,991

(22) PCT Filed: Dec. 19, 2016

(86) PCT No.: PCT/EP2016/081673
§ 371 (c)(1),
(2) Date: Jun. 13, 2018

(87) PCT Pub. No.: WO2017/108663
PCT Pub. Date: Jun. 29, 2017

(65) Prior Publication Data
US 2018/0371534 A1 Dec. 27, 2018

(30) Foreign Application Priority Data
Dec. 22, 2015 (IT) .................. 102015000086668

(51) Int. Cl.
*C12Q 1/68* (2018.01)
*C12Q 1/6844* (2018.01)
*C12Q 1/6853* (2018.01)

(52) U.S. Cl.
CPC ......... *C12Q 1/6844* (2013.01); *C12Q 1/6853* (2013.01); *C12Q 2525/161* (2013.01); *C12Q 2525/301* (2013.01); *C12Q 2527/101* (2013.01); *C12Q 2531/119* (2013.01); *C12Q 2565/101* (2013.01)

(58) Field of Classification Search
CPC ............ C12Q 1/6844; C12Q 2525/161; C12Q 2525/301; C12Q 2531/119; C12Q 2565/101
See application file for complete search history.

(56) References Cited

U.S. PATENT DOCUMENTS

| 10,724,091 | B1* | 7/2020 | Meagher | .............. | C12Q 1/6853 |
| 2013/0171643 | A1* | 7/2013 | Kubota | .............. | C12Q 1/6853 |
| | | | | | 435/6.11 |
| 2016/0053309 | A1* | 2/2016 | Kitani | .............. | C12Q 1/6853 |
| | | | | | 506/9 |

FOREIGN PATENT DOCUMENTS

| WO | WO 2011/163425 | 12/2011 |
| WO | WO 2014/157377 | 10/2014 |
| WO | WO 2015/127201 | 8/2015 |

OTHER PUBLICATIONS

Chen, Q. et al. (1997) "Fluorescence Resonance Energy Transfer Study of Shape Changes in Membrane-Bound Bovine Prothrombin and Meizothrombin," Biochemistry 36(15):4701-11.
Chou, P.-H. et al. (2011) "Real-Time Target-Specific Detection of Loop-Mediated Isothermal Amplification for White Spot Syndrome Virus Using Fluorescence Energy Transfer-Based Probes," J. Virol. Methods. 173(1):67-74.
Clegg, R.M. (1995) "Fluorescence Resonance Energy Transfer," Curr. Opin. Biotechnol. 6:103-110.
Eiken website (loop) http://loopamp.eiken.co.ip/e/lamp/loop.html (2005) 2 pages.
Eiken website (primer) http://loopamp.eiken.co.ip/e/lamp/primer.html (2005) 2 pages.
Gandelman, O.A. et al.( 2010) "Novel Bioluminescent Quantitative Detection of Nucleic Acid Amplification in Real-Time," PLoS One 5(11): e14155 (pp. 1-13).
International Search Report PCT/EP2016/081673 (dated 2017) 6 pages.
Le Reste, L. et al. (2012) "Characterization of Dark Quencher Chromophores as Nonfluorescent Acceptors for Single Molecule FRET," Biophysical J. 102:2658-2668.
Mair, G. et al. (2013) "Isothermal Loop-Mediated Amplification (LAMP) for Diagnosis of Contagious Bovine Pleuro-Pneumonia," BMC Veterinary Research 9:108 (pp. 1-8).
Mori, Y. et al. (2001) "Detection of Loop-Mediated Isothermal Amplification Reaction by Turbidity Derived From Magnesium Pyrophosphate Formation," Biochem. Biophys. Res. Commun. 289: 150-154.
Notomi, T. et al (2000) "Loop-Mediated Isothermal Amplification of DNA," Nucleic acids Res. vol. 28(12)-e63 (pp. 1-7).
Tomita, N. et al. (2008) "Loop-Mediated Isothermal Amplification (LAMP) of Gene Sequences and Simple Visual Detection of Products," Nat. Protoc. 3:877-882.
Written Opinion PCT/EP2016/081673 (dated 2017) 6 pages.
Zerilli, F. et al. (2010) "Methylation-Specific Loop Mediated Isothermal Amplification for Detecting Hypermethylated DNA in Simplex and Multiplex Formats," Clin. Chem. 56:1287-1296.
Zhang, X. et al. (2013) "Development of a Real-Time Fluorescence Loop Mediated Isothermal Amplification Assay for Rapid and Quantitative Detection of Fusarium oxysporum f. sp. Cubense Tropical Race 4 in Soil," PLoS One 8(12):e82841 (pp. 1-10).

* cited by examiner

*Primary Examiner* — David C Thomas
(74) *Attorney, Agent, or Firm* — Jeffrey I. Auerbach; AuerbachSchrot LLC

(57) ABSTRACT

The invention concerns a method for detecting isothermal loop-mediated (LAMP) amplification of a target nucleic acid sequence which is based on the fluorescence resonance energy transfer (FRET) mechanism. The invention also concerns a set of oligonucleotides and a kit adapted for carrying out the LAMP-FRET method of the invention.

Figure 1:
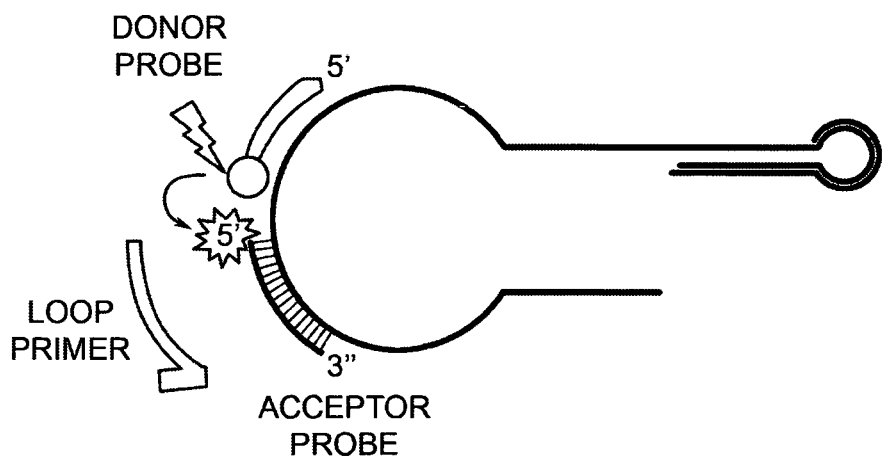
Figure 1:
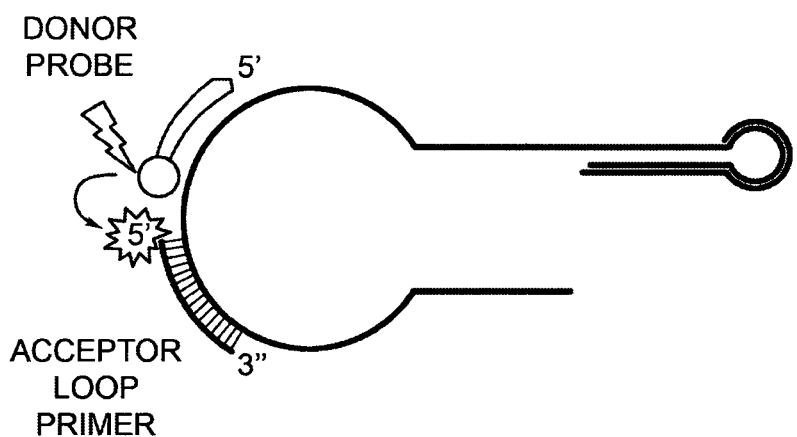
Figure 1:
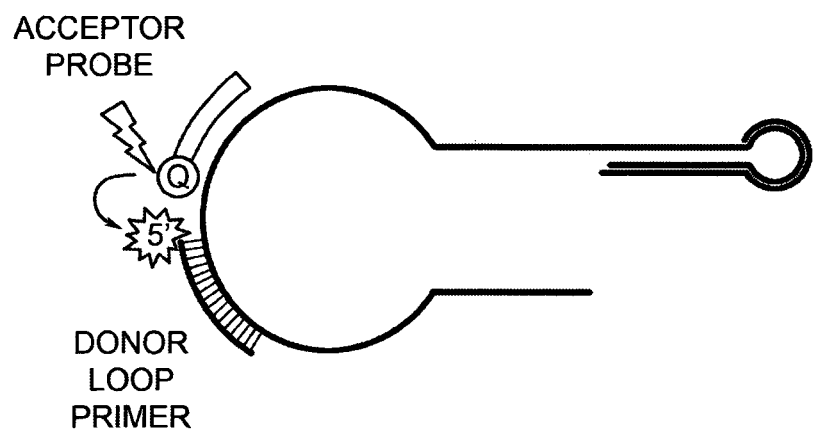

12 Claims, 5 Drawing Sheets
Specification includes a Sequence Listing.

A. FRET

B. Intercalating dye

METHOD OF FLUORESCENT DETECTION OF ISOTHERMAL LOOP-MEDIATED AMPLIFICATION (LAMP) OF A TARGET NUCLEIC ACID, OLIGONUCLEOTIDES AND KITS THEREOF

CROSS-REFERENCE TO RELATED APPLICATIONS

This application is a § 371 National Stage Application of PCT/EP2016/081673 (filed on Dec. 19, 2016; pending), which application claims benefit of IT Patent Application No. 102015000086668 (filed on Dec. 22, 2015). Each of these applications is hereby incorporated by reference in its entirety.

REFERENCE TO SEQUENCE LISTING

This application includes one or more Sequence Listings pursuant to 37 C.F.R. 1.821 et seq., which are disclosed in computer-readable media (file name: Sequence_Listing_PC1504EC.txt, created on Jun. 5, 2018, and having a size of 3,033 bytes), which file is herein incorporated by reference in its entirety.

The present invention relates to a method for detecting nucleic acid amplification by means of loop-mediated isothermal amplification (LAMP), as well as to a set of oligonucleotides and a kit for carrying out the method of the invention.

Loop-mediated isothermal amplification (LAMP) is a recently developed method of nucleic acid amplification via an autocyclic strand displacement reaction, which is performed at a constant temperature, usually between 60° C. and 65° C. (Notomi T. et al 2000. Nucleic acids Res. Vol. 28(12)-e63). This technology employs a DNA polymerase with strand displacement activity and a set of four oligonucleotides, termed inner and outer primers, specifically designed to recognize six different recognition sites on the target nucleic acid. The two outer primers play a role in strand displacement during the non-cyclic step only whereas the inner primers include both sense and antisense sequences and contribute to formation of typical LAMP amplification products having stem-loop structures.

In addition to the four oligonucleotide primers, the LAMP assay may involve the use of two additional primers, the so-called loop primers, to improve amplification efficiency, thereby resulting in a total of six primers per target sequence. Such a combination of different primers, which span eight distinct sequences on the target nucleic acid, provides for a remarkable degree of assay specificity.

LAMP-based technology possesses the advantages of high sensitivity, rapid amplification, and simple operation. LAMP assay results in a highly efficient synthesis of amplified products, which is at least 50 times higher than the one obtained by classical PCR reactions in identical volumes. In addition, the ability to amplify nucleic acid under isothermal conditions enables the use of simple and cost-effective equipment, without the requirement of thermal cycling. In LAMP assays, both the amplification and detection of specific amplicons may be accomplished in a single step, thereby significantly decreasing the reaction time compared to a standard RT-PCR.

Several methods have been employed for the detection of LAMP amplification products including visual examination or turbidity monitoring of precipitated magnesium pyrophosphate (Tomita N., et al. 2008. *Nat. Protoc.* 3:877-882; Mori Y., et al. 2001. *Biochem. Biophys. Res. Commun.* 289:150-154), fluorescence detection of double-stranded DNA (dsDNA) with an intercalating fluorophore (Zhang X, et al. 2013, *PLoS One* 8(12):e82841; Mair G. et al. 2013, *BMC Veterinary Research* 9:108.), bioluminescence reporting through pyrophosphate conversion (Gandelman O A., et al. 2010, *PLoS One* 5(11): e14155).

Known strategies for the indirect detection of LAMP amplification rely essentially on the formation of pyrophosphate as a reaction byproduct. As LAMP reactions proceed, pyrophosphate ions are released by incorporation of deoxynucleotide triphosphates (dNTPs) into the DNA strand during nucleic acid polymerization and these ions react with divalent metal ions, particularly magnesium ions, present in the reaction mix to produce white, insoluble magnesium pyrophosphate precipitate (Mori Y., et al. 2001. *Biochem. Biophys. Res. Commun.* 289:150-154). This product results in a progressive increase in the turbidity of the reaction solution and pyrophosphate precipitates can be measured quantitatively in terms of turbidity or observed by the naked eye as a pellet after centrifugation. In an alternative format, the detection of LAMP amplification is achieved through the incorporation of manganese ions and calcein in the reaction. Calcein's fluorescence is naturally quenched by binding of manganese ions. Pyrophosphate production as a byproduct of LAMP reaction removes manganese ions form the buffer through precipitation, and the increased turbidity coupled with restored calcein fluorescence enables an easy visual read-out upon excitation with either visible or UV light (Tomita N., et al. 2008. *Nat. Protoc.* 3:877-882). In still another detection format, the enzymatic conversion of pyrophosphate into ATP, which is produced during DNA synthesis, is monitored through the bioluminescence generated by thermostable firefly luciferase (Gandelman O A., et al. 2010, *PLoS One* 5(11): e14155).

LAMP amplification products may also be detected through direct approaches which act via fluorescence reporting. The majority of such approaches are based on the use of intercalating dyes, such as ethidium bromide, SYBR Green, EvaGreen and YO-PRO-I (Zhang X, et al. 2013, *PLoS One* 8(12):e82841; Mair G. et al. 2013, *BMC Veterinary Research* 9:108.). Typically, intercalating dyes are non-sequence-specific fluorescent dyes that exhibit a large increase in fluorescence emission upon binding into dsDNA. Such property may be used to monitor the nucleic acid amplification in real time by continuously measuring the fluorescence during the LAMP reaction. However, since intercalating dyes bind to any dsDNA, the implementation of such dyes in real-time amplification methods does not allow to discriminate between specific target amplification products and co-produced artifacts, such as non-specific amplicons and primer-dimers, which may result in an overestimation of the target concentration. Consequently, the detection of nucleic acid amplification by intercalating dyes requires extensive optimization and follow-up assays are usually needed to validate the results.

Fluorescence-based detection of LAMP amplification may also rely on the mechanism of Förster resonance energy transfer (FRET) (Chen Q, et al. 1997 Biochemistry 36(15): 4701-11). FRET is a distance-dependent interaction between the electronic excited states of two chromophores in which excitation is transferred from a donor molecule to an acceptor molecule. When the acceptor itself is a fluorophore, the FRET-induced acceptor excited state can subsequently relax by acceptor fluorescence emission. The acceptor chromophore does not need itself to be fluorescent and FRET systems with dark acceptors have been largely implemented in recent years. For instance, dark quenchers may be used which are chromophores that can be excited to higher electronic states upon absorption of photons and relax to the ground state preferentially by nonradiative processes, thereby remaining dark (Le Reste L. et al. 2012. *Biophysical Journal* 102: 2658-2668). Acceptance of donor energy by a FRET acceptor requires that the absorbance spectrum of the acceptor chromophore overlaps the emission spectrum of the donor chromophore. Further, the donor and acceptor chromophores need to be in close proximity for energy transfer to occur and the efficiency of such transfer is highly dependent on the sixth power of the distance between the two chromophores (Clegg R M. 1995 Curr. Opin. Biotechnol. 6: 103-110).

Chou et al. (Chou P H, et al. 2011 J Virol Methods. 173(1):67-74) describe an assay for the diagnosis of White spot syndrome virus (WSSV) infections in shrimps, which combines LAMP and FRET hybridization probe technology. More specifically, in addition to the standard set of LAMP primers, including the so-called loop-primers, the assay by Chou et al. involves the use of two fluorescent probes labeled at the 3'- and 5'-end sequence, respectively (FIG. 1A), which hybridize in a head to tail configuration to the single-stranded loop region present in the intermediate LAMP products. By bringing the two fluorophores in close proximity, energy transfer occurs and a real-time FRET signal is generated during the isothermal amplification reaction. FIG. 1A illustrates a LAMP intermediate product, wherein one loop end has been enlarged to show in detail the hybridization of the oligonucleotides employed in the FRET assay detection step.

Among detection methods based on fluorescence energy transfer, hybridization-induced fluorescence quenching has also been exploited in LAMP applications, particularly through the principle of guanine quenching (Zerilli et al. 2010. Clin Chem 56:1287-96). In such an approach the fluorescence emitted by a 5' labeled LAMP loop primer is progressively quenched upon hybridization to a complementary target sequence containing a guanine. The extent of the quenching effect depends on the number and positions of the adjacent G bases on the complementary target sequence. As target sequences accumulate in a real-time LAMP assay, quantitative measurements of nucleic acid amplification may be achieved by monitoring the amount of quenched fluorescence as a consequence of the incorporation of the dye-labeled loop primer in the amplification products. Such a strategy, however, suffers of the disadvantage of being dependent on the specific nucleotide sequence of the target nucleic acid and is limited by the presence and/or position of guanine nucleotides within such sequence.

In recent years, large efforts have been directed toward adapting isothermal methods such as LAMP into molecular diagnostic assays, taking advantage of the simplified testing equipment which does not require temperature cycling and allows versions to be produced for use in quite elementary health care settings. As isothermal techniques are being adopted as diagnostic tools, an essential requirement for such techniques is their ability to generate a patient result in a very short time, in order to provide reliable and rapid assistance in clinical decision making for every stage in patient care, i.e. early diagnosis, risk assessment, screening, staging and prognosis, therapy selection and monitoring. For instance, early diagnosis of hematological malignancies such as acute leukemia is crucial to ensure a good prognosis for patients, since a timely, treatment may be crucial and decisive in the disease management.

Thus, there exists a need in the art to develop loop-mediated isothermal amplification methods capable of accomplishing a rapid detection of target nucleic acid sequences without affecting critical assay parameters such as specificity, sensitivity and accuracy.

This and other needs are met by the method, set of oligonucleotides and kit as defined in the appended claims, which form an integral part of the description.

As further illustrated in the experimental section below, the present invention provides a method for the detection of LAMP amplification of target nucleic acid sequences, which makes use of the principle of fluorescence energy transfer. The method of the present invention employs a DNA polymerase having strand displacement activity and a set of oligonucleotide LAMP primers consisting of two outer primers, namely F3 and B3, two inner primers, namely FIP and BIP, one or two loop primers, namely LF and/or LB, and one nucleic acid probe. A description of the features and function of the LAMP primers and loop primers is found e.g. at the Eiken website (loopamp.eiken.co.jp/e/lamp/primer.html; loopamp.eiken.co.jp/e/lamp/loop.html).

According to the present invention, the first inner primer FIP consists of a 3' nucleic acid sequence designated as F2, which is complementary to a F2c region of the target nucleic acid sequence, and a 5' nucleic acid sequence designated as F1c. The second inner primer BIP consists of a 3' nucleic acid sequence designated as B2, which is complementary to a B2c region of the target nucleic acid sequence, and a 5' nucleic acid sequence designated as B1c. The F2c and B2c regions are non overlapping regions located on opposite strands of the target nucleic acid sequence.

The external primer F3 consists in the F3 region that is complementary to the F3c region; the external primer B3 consists in the B3 region that is complementary to the B3c region.

As mentioned above, the method of the present invention employs one or two loop-primers, LF and/or LB. Typically, when used in a LAMP reaction, loop-primers hybridize to the single-stranded loop region present in the intermediate LAMP products and provide an increased number of starting points for DNA synthesis. According to the invention, either the LF loop primer or the LB loop-primer, if present, is labeled at its 5'-end with at least one fluorescent moiety.

Compared with standard LAMP technology, the method of the invention involves the use of an additional oligonucleotide, more particularly a nucleic acid probe, which is labeled at its 3'-end with at least one chromophore moiety. Said nucleic acid probe is capable of hybridizing to the target nucleic acid sequence 5' to the labeled LF or LB primer so that, when hybridized to the target nucleic acid sequence, the 3'-end of the nucleic acid probe is in close proximity to the 5'-end of the labeled LF or LB primer.

In the present description, a nucleic acid sequence (either a primer or a probe) that is capable of hybridizing to a given target nucleic acid sequence is for example complementary to said nucleic acid sequence.

It is noted that a "close proximity" of said labeled loop-primer and said labeled nucleic acid probe occurs only during the amplification phase of a LAMP reaction when the loop-primer is incorporated and extended in the LAMP amplification product.

In a first embodiment shown in FIG. 1B, the method according to the invention employs a loop-primer labeled at its 5'-end with at least one acceptor fluorescent moiety in combination with a nucleic acid probe labeled at its 3'-end with at least one donor fluorescent moiety. FIG. 1B illustrates a LAMP intermediate product, wherein one loop end has been enlarged to show in detail the hybridization of the oligonucleotides employed in the FRET assay detection step.

The labeled loop-primer may be either LF or LB (when LB is present). According to the invention, upon hybridization of said oligonucleotides to the target nucleic acid sequence during the LAMP reaction, the donor fluorescent moiety at the 3'-end of the nucleic acid probe is brought in close proximity to the acceptor fluorescent moiety at the 5'-end of the LF or LB primer. Fluorescence energy transfer occurs between such moieties and, as a result, a change in a fluorescent parameter is generated and detected. Such a change is an indication of DNA amplification in that it is generated upon incorporation of the labeled loop-primer in the LAMP amplification product and subsequent primer extension.

In another embodiment shown in FIG. 10, the method of the present invention uses either the LF or LB loop-primer labeled at its 5'-end with at least one donor fluorescent moiety in combination with a nucleic acid probe labeled at its 3'-end with at least one quenching moiety. According to the invention, when the 3'-end of the labeled nucleic acid probe and the 5'-end of the labeled loop-primer are brought in close proximity on the target nucleic acid sequence during LAMP amplification, the quenching moiety functions as an acceptor by absorbing the energy emitted by the donor moiety and dissipating such energy as heat. An associated change in a fluorescence parameter may therefore be detected as an indication of DNA amplification during the LAMP reaction. FIG. 1C illustrates a LAMP intermediate product, wherein one loop end has been enlarged to show in detail the hybridization of the oligonucleotides employed in the FRET assay detection step.

The performance of the method of the invention according to the first embodiment as above defined was evaluated by the present inventors in comparison with prior art fluorescence-based LAMP assays, more specifically the FRET-based LAMP assay described by Chou et al. and the LAMP system making use of intercalating dyes.

In order to compare the performance of the LAMP method of the invention with the assay by Chou et al., a dilution design was used and titration series ranging from $2\times10^1$ copies/µL to $2\times10^6$ copies/µL of a denatured plasmid containing a WSSV genomic fragment were subjected to LAMP amplification on a Rotor-Gene Q instrument (Qiagen). In particular, comparative analysis was performed on the dilutions corresponding to $2\times10^3$ copies/µL and $2\times10^6$ copies/µL, respectively. The amplification of the target produced an increasing fluorescent signal with a sigmoidal shape that was detected by setting readings with 1 minute step.

By using the Rotor-Gene Software the normalized signal was generated, and by setting a fluorescence threshold at 0.2 corresponding at around 50% of the fluorescence increment, the Threshold time (minutes) was identified to detect the target amplification.

Figure 2:
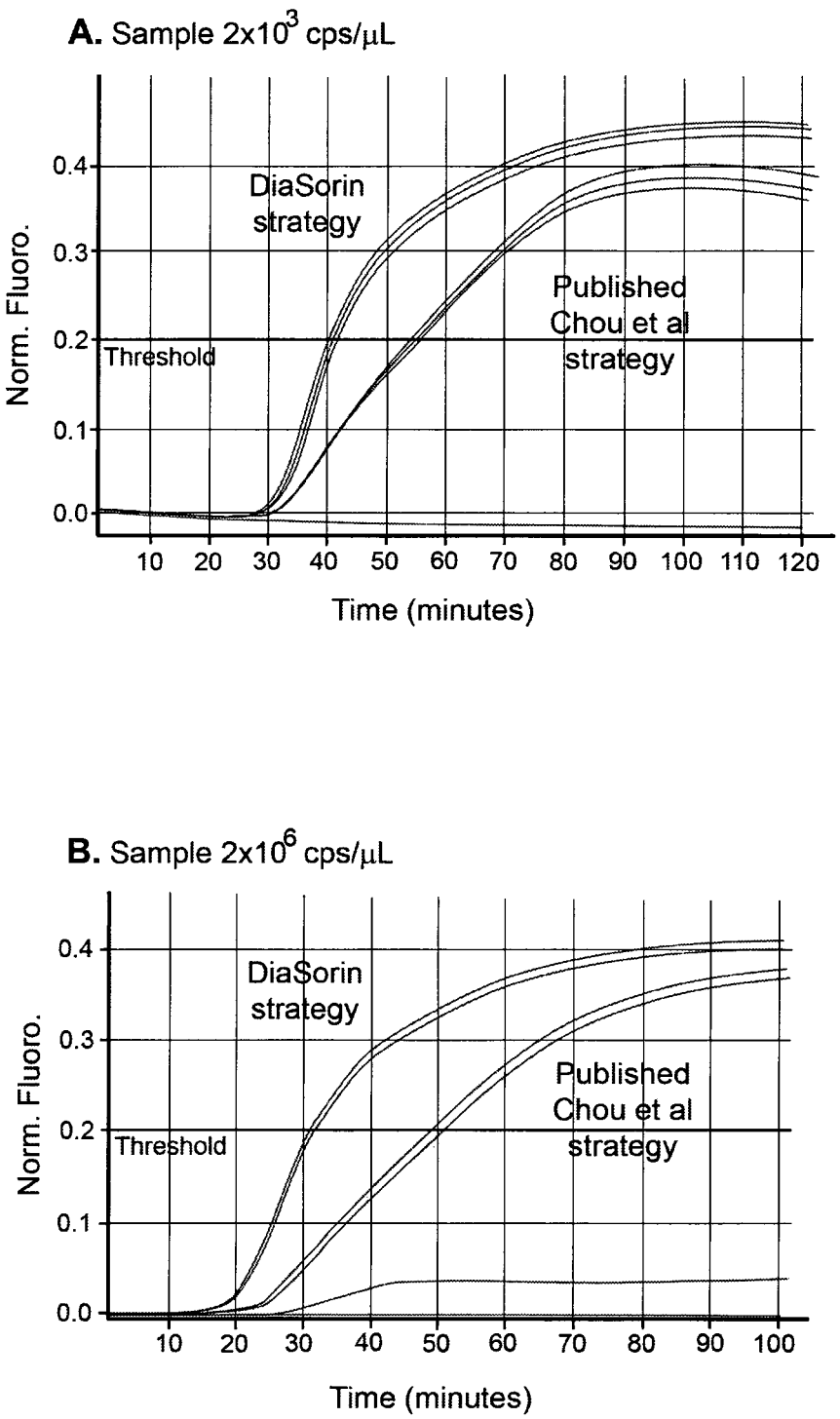

A comparative analysis of the threshold time generated for these diluted samples by each of the LAMP methods under examination showed that the method of the invention achieves a significant earlier detection of the target nucleic acid sequence compared to the method by Chou et al (shown in FIG. 2).

Moreover, the statistical significance of the difference in detection time measured between the LAMP methods under examination was calculated by performing a Student's t-test, which provided a p-value lower than 0.05.

To further assess the method of the invention for the ability to detect target nucleic acids in a natural matrix, the experimental procedure as above-described was applied to the same dilution of the WSSV plasmid ($2\times10^3$ copies/µL and $2\times10^6$ copies/µL) in human genomic DNA (20 ng/µL). LAMP amplification reactions performed on such dilutions revealed that the presence of material, such a genomic DNA, which may cause interference, did generate delay in the detection of target nucleic acid sequence by both the methods. Moreover, target detection was accomplished by the method of the invention at 10 or more minutes earlier than the detection achieved by the LAMP system by Chou et al.

In assay validation, linearity represents one of the most relevant indicators of assay accuracy, in that it measures the ability of the procedure to return values that are directly proportional to the concentration of the target analyte in the test samples. In the present study, LAMP amplification data obtained by applying either the method of the invention or the method by Chou et al. on the above-indicated sample titration series were subjected to linear regression analysis.

Figure 3:
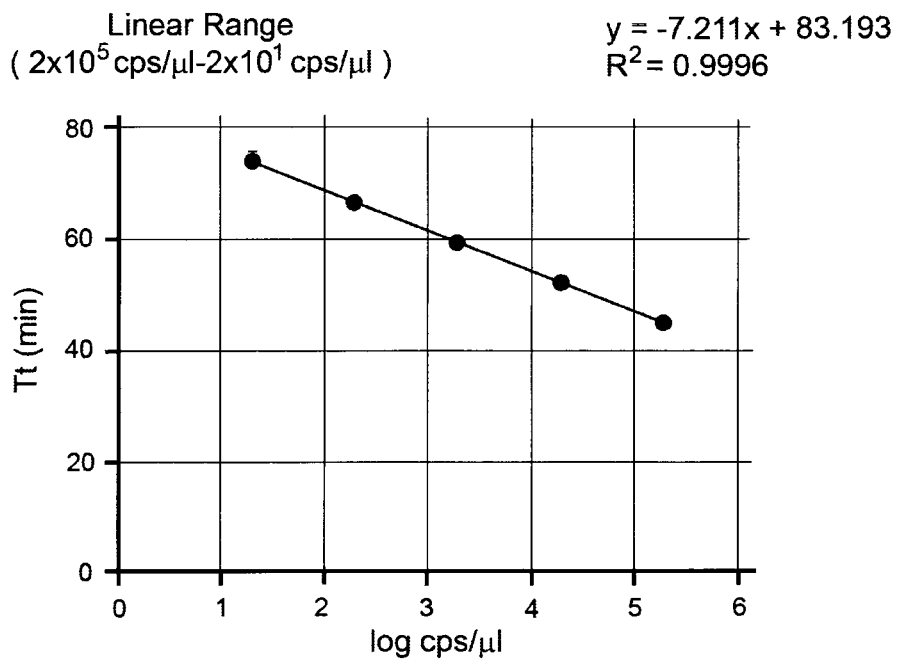
Figure 3:
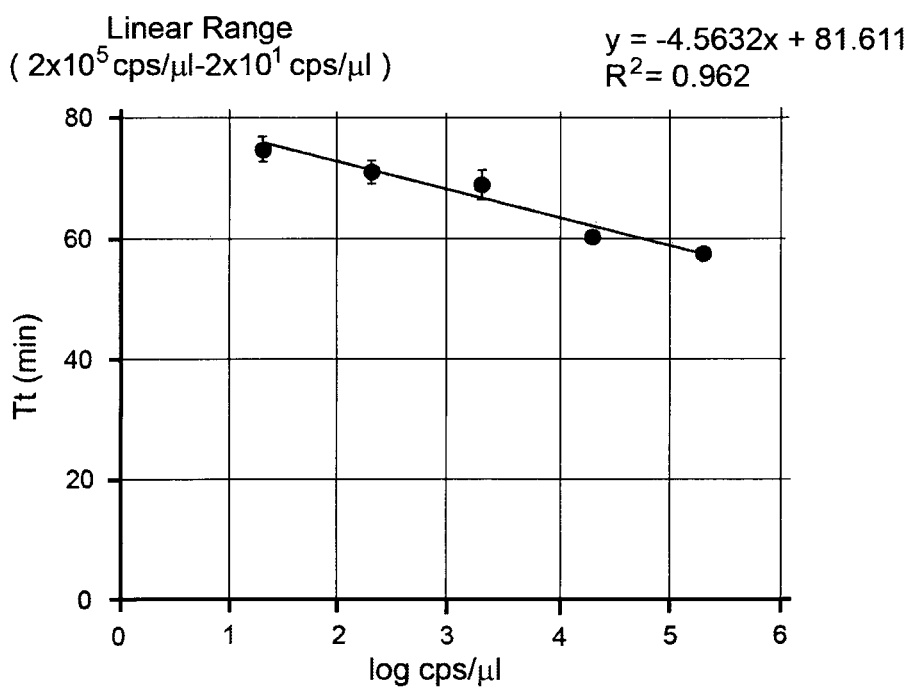

In FIG. 3, the threshold time (indicated in minutes) is plotted against the concentration of the plasmid nucleic acid target, expressed as copies/µL, for both (A) the LAMP method of the invention and (B) the LAMP assay by Chou et al. Compared with the results obtained with the LAMP-FRET procedure by Chou et al., this figure shows that the method of the present invention provides a superior linearity since a correlation coefficient ($R^2$)=0.99, and a slope=−7.2 were calculated for the regression line. Furthermore, the determination of such a good linearity is indicative of assay precision as well, as it implies high reproducibility among replicate measurements.

Figure 4:
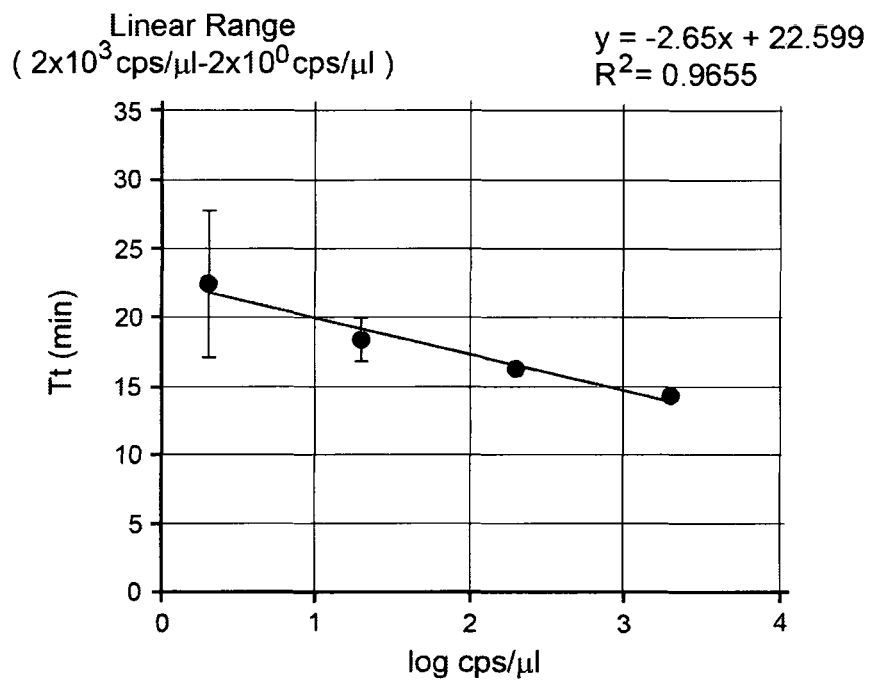
Figure 4:
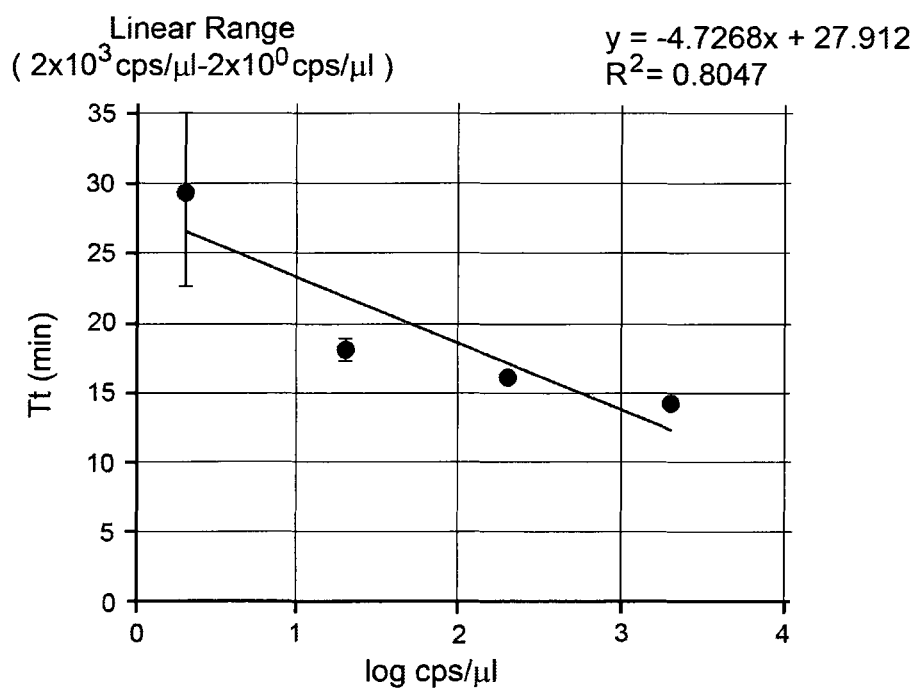

The present inventors performed a further evaluation by comparing the performance of the method of the invention with a LAMP assay that involves the use of intercalating dyes for fluorescence detection. Linear regression analysis was applied on the LAMP amplification data obtained by carrying out either the method of the present invention or the intercalating dye-based assay on ten-fold serially diluted plasmid DNA samples containing the MYH11 gene. The results of linear regression analysis are shown in FIG. 4. This figure shows the threshold time (indicated in minutes) plotted against the concentration of the plasmid nucleic acid target, expressed as copies/uL, for both (A) the LAMP method of the invention and (B) the intercalating dye assay. The data obtained confirm a significant higher linearity of the method of the present invention compared with the LAMP system using the YO-PRO intercalating dye ($R^2$=0.97 versus $R^2$=0.80).

Along with the better assay linearity, a higher analytical sensitivity and wider linearity range were observed for the method of the present invention. Finally, compared to the intercalating dye-based LAMP, the method of the present invention which employs a labeled loop-primer/probe FRET pair results in enhanced assay specificity, since intercalating dyes such as YO-PRO emit a fluorescence signal upon binding to any double-stranded DNA, irrespective of the specific nucleotide sequence.

In the present study, performance assessment of the second embodiment of the method of the present invention was performed in comparison with a LAMP assay involving the mechanism of fluorophore guanine quenching for the detection of amplification signal. The latter assay is based on the use of a loop-primer labeled with a fluorophore whose signal emission is quenched by a guanosine nucleotide present on the template sequence.

LAMP amplification experiments performed by the present inventors on the model GUS beta gene (amplified region corresponding to the region exon 3-exon 4) revealed that by using a quenching probe the detection of this amplicon is achieved within the same threshold time (about 29 minutes). Hence, such a result demonstrates that the presence of a "quencher probe" in the LAMP reaction does not affect the detection kinetics. In contrast, the additive quenching effect of the labeled probe improved the quenching obtained with the guanine quenching method alone.

Figure 5:
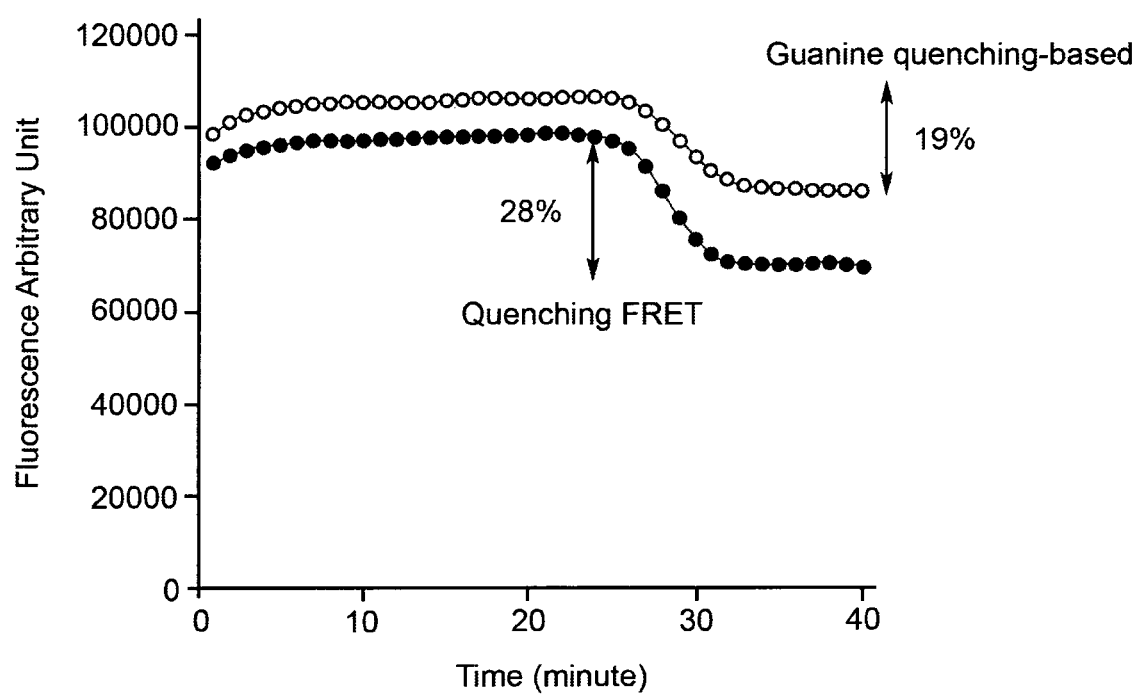

As shown in FIG. 5, the method of the present invention generated a significantly larger degree of quenching (28% instead of 19% of intensity, $p<0.05$), with an improvement of more than 40% in terms of quenching. In this figure, fluorescence (expressed as arbitrary units) is plotted against the reaction time (indicated in minutes). The upper dotted line represent guanine quenching-based LAMP, the lower dotted line represent the Quenching FRET LAMP. The Quenching rate was calculated as equal to 100−((Min/Max)*100).

In the method of the present invention, the amplification of the target nucleic acid sequence leads to a detectable change in a fluorescence parameter. For example, the detection step may reveal an increase in acceptor fluorescence intensity when energy transfer occurs between the donor moiety at the 3'-end of the nucleic acid probe and the acceptor moiety at the 5'-end of the LF or LB loop primer. As an alternative, a decrease in the fluorescence intensity of the donor moiety at the 5'-end of the labeled loop-primer may be measured when the acceptor moiety at the 3'-end of the nucleic acid probe plays the role of a quencher.

According to the present invention, other fluorescence parameters which are affected by the proximity of the donor and acceptor fluorescent moieties may also be monitored, including, for example, a change in the ratio of donor and/or acceptor fluorescence intensities or fluorescence life-time.

As outlined above, acceptance of donor energy by a FRET or quenching/acceptor moiety requires close proximity between said molecules and the efficiency of FRET is very sensitive to the distance and relative orientation between donor and acceptor. According to the method of the present invention, upon hybridization to the target nucleic acid sequence, the distance between the labeled 3'-end of the nucleic acid probe and the labeled 5'-end of the loop primer should preferably be comprised between zero and 6 nucleotides, for example zero, 1, 2, 3, 4, 5 or 6 nucleotides.

According to the present invention, the nucleic acid probe comprises at least one chromophore moiety—either a donor fluorescent moiety or a quencher moiety—linked to its 3'-end. Such a chromophore acts as a blocker of DNA synthesis in that it makes the 3'-terminal of the nucleic acid probe no longer available as origin for DNA polymerization.

Conversely, in the present invention the fluorescent moiety carried by the labeled loop-primer—either a donor or an acceptor moiety—is linked to the 5'-end of said oligonucleotide in order to avoid any interference with DNA synthesis during LAMP reaction. Specifically, the labeled loop-primer according to the invention has a 3'-free hydroxyl group which serves as origin for the synthesis of the complementary DNA strand.

Since target detection is achieved directly via signal components linked on specific oligonucleotides, the method of the present invention provides a sequence-specific detection technology. According to the invention, the labeled nucleic acid probe and labeled loop-primer may be designed to tolerate sequence variations for detection of diverse DNA or RNA sequences or to differentiate between sequence polymorphism. In addition, it is understood that hybridization between the nucleic acid probe and loop-primer and their respective complementary sequences on the target nucleic acid may be enhanced by incorporating in such oligonucleotides certain types of modified nucleotides, for example, 2'-O-methylribonucleotides or nitropyrole-based nucleotides, or certain types of nucleic acid analogs with non-natural backbone, for example PNA (peptide nucleic acid) or LNA (locked nucleic acid). The use of nucleic acid analogs in nucleic acid amplification methods is well established and known to the person skilled in the art.

In the context of the present invention, the term "target nucleic acid sequence" refers to nucleic acid sequences to be amplified and detected. These include the original nucleic acid sequence to be amplified, its complementary second strand and either strand of a copy of the original sequence which is produced by replication or amplification. The target nucleic acid can originate from a variety of sources. For example, target nucleic acids can be naturally occurring DNA or RNA isolated from any source, recombinant molecules, cDNA, or synthetic analogs, as known in the art. In some embodiments, the target nucleic acid sequence may comprise one or more single-nucleotide polymorphisms (SNPs), allelic variants, and other mutations such as deletion mutations, insertion mutations, point mutations. In other embodiments, the target nucleic acid sequence may comprise a junction sequence of a fusion gene, possibly associated with cancer. In yet another embodiment, the target nucleic acid sequence may originate from a microorganism, including specific clones or strains of microorganisms, possibly involved in inducing diseases in human beings and animals.

The method of the present invention is also suitable for quantitatively determine the amount of target nucleic acid sequences in a sample. In a preferred embodiment of the invention, the quantification of a target nucleic acid sequence is accomplished via the generation of a standard curve by plotting a graph of known copy number (or concentration) of such target nucleic acid sequence against LAMP assay time to positivity. Quantification of unknown target copy number (or concentration) in the test samples may be extrapolated from the standard curve on the basis of the time to positivity measured in the unknown sample.

Another aspect of the present invention is a set of oligonucleotides for detecting loop-mediated isothermal amplification (LAMP) of a target nucleic acid sequence, the set consisting of a first outer primer F3, a second outer primer B3, a first inner primer FIP, a second inner primer BIP, a first loop-primer LF, a second loop-primer LB and one nucleic acid probe, all as defined above with reference to the method of the invention. In a first embodiment, either the LF loop primer or the LB loop primer (when LB is present) is labeled at its 5'-end with at least one fluorescent acceptor moiety and the nucleic acid probe is labeled at its 3'-end with at least one fluorescent donor moiety.

According to a second embodiment of the invention, either the loop primer LF or the LB loop primer (when LB is present) is labeled at its 5'-end with at least one fluorescent donor moiety and the nucleic acid probe is labeled at its 3'-end with at least one quenching moiety.

A requirement for Förster resonance energy transfer to occur is that the emission spectrum of a first donor moiety overlaps with the absorption spectrum of a second acceptor moiety, so that excitation by lower-wavelength light of the donor moiety is followed by transfer of part of the excitation energy to the acceptor moiety.

There are many chromophores which may serve as either a donor, an acceptor or a quencher in the present invention.

According to a preferred embodiment, the fluorescent donor moiety is selected from the group consisting of Fluorescein, BODIPY FL, Alexa555, ATTO550, Cy3, FAM, TET, HEX, JOE, VIC, Cy3, NED, Quasar 570, Oyster 556, TAMRA and/or the fluorescent acceptor moiety is selected from the group consisting of Cy5.5, Cy5, ATTO647N, Alexa 647, ROX, LC red 610, Texas red, LC red 640, LC red 670, Quasar 670, Oyster 645, LC red 705.

In another preferred embodiment, the fluorescent donor moiety is selected from the group consisting of Fluorescein, BODIPY FL, Alexa555, ATTO550, Cy3, FAM, TET, HEX, JOE, VIC, Cy3, NED, Quasar 570, Oyster 556, TAMRA, Cy5.5, Cy5, ATTO647N, Alexa 647, ROX, LC red 610, Texas red, LC red 640, LC red 670, Quasar 670, Oyster 645, LC red 705 and/or the quencher moiety is selected from the group consisting of DDQ-I, Dabcyl, Eclipse, Iowa Black FQ, BHQ-1, BHQ-2, BHQ-3, QSY-7, DDQ-II, Iowa Black RQ, QSY-21, ATTO 540Q, ATTO 580Q, ATTO 612Q.

Especially preferred is the donor/acceptor pair BODIPY FL/ATTO647N and the donor/quencher pair BODIPY 630/BHQ3.

In yet another embodiment, the nucleic acid probe and/or the loop primer are labeled with more than one fluorescent moiety, preferably two moieties.

In the most preferred embodiment, the FRET donor/acceptor pair consists of two BODIPY FL moieties and one ATTO647N moiety, respectively. The selection of suitable donor/acceptor moieties pair or donor/quenching moieties pair suitable for the present invention is well within the knowledge of the person skilled in the art.

As mentioned above, a further aspect of the present invention is a kit for detecting loop-mediated isothermal amplification (LAMP) of a target nucleic sequence, the kit comprising the set of oligonucleotides as defined above, as well as one or more DNA polymerases having strand displacement activity. The DNA polymerase is preferably selected from the group consisting of Bst large fragment polymerase, Bst 2.0, Bst 3.0, Bca (exo-), Vent, Vent (exo-), Deep Vent, Deep Vent (exo-), Φ29 phage, MS-2 phage, Z-Taq, KOD, Klenow fragment, GspSSD, GspF, OmniAmp Polimerase, SD Polimerase and any combination thereof. The most preferred DNA polymerase is the Bst large fragment polymerase.

The following experimental section is provided purely by way of illustration and is not intended to limit the scope of the invention as defined in the appended claims.

EXPERIMENTAL SECTION

Example 1

Comparison of the LAMP Method of the Invention with the LAMP Assay by Chou et al Sample Preparation To compare the LAMP method of the invention with the LAMP assay described in Chou et al., a suitable target nucleic acid sequence was prepared. Briefly, a 350-bp DNA fragment derived from the White spot syndrome virus (WSSV) genome (nt226681-227934, GenBank AF332093.1) was cloned into the pMA-T vector (GE-NEART) by using the Sfi I/Sfi I restriction site combination to provide the positive control. Ten-fold dilution series in the range of approximately $2 \times 10^6$ copies/μL to $2 \times 10^1$ copies/μL were prepared for the recombinant WSSV plasmid.

Two different plasmid dilution series were prepared using as diluent either Tris-HCl mM, pH 8.5 alone, or this buffer additionally containing human genomic DNA (20 ng/μl).

In the present study, the analyzed plasmid dilutions were denatured at 100° C. for 10 minutes. After denaturation, the plasmid samples were immediately placed on ice for 10 minutes.

LAMP Reaction

The LAMP oligonucleotide primers and probes employed for the comparative analysis were designed as described in Chou et al., and are listed in Table 1 below.

TABLE 1

| Oligo name | Sequence (5'->3') | SEQ ID NO: |
|---|---|---|
| F3 | TGATTCAGATGGCATGGATACTT (Forward outer primer) | 1 |
| B3 | CCGATACTGCCATTGAAAGC (Reverse outer primer) | 2 |
| FIP | TGTTATGGTAGTGAACCCCTTTGCACGACTTATCATTCAAGACATCAAT (Forward inner primer) | 3 |
| BIP | GGAAGAAAGATACAAGCCCATTGGCGCTCCCTTACCACCTTCCTTAATC (Reverse inner primer) | 4 |
| LoopB | GCCATTGAAGCAGTGTTGGGAT (Reverse loop) | 5 |
| LoopF | GATCGTTAACAACAACAATACTGGA (Forward loop) | 6 |
| LCF | CACCCACAGCGGCTCTTGC-Fluorescein (3' fluorescein labeled FRET probe) | 7 |
| LCQ | LC640-CGTTCGCCATTGAAGCAGTGTTGG-Phosphate (5'LC640 labeled FRET probe) | 8 |

Table 1 contains the full set of oligonucleotides used in the assay by Chou et al. The set of oligonucleotides employed in the LAMP method according to the invention differs from the oligonucleotide set by Chou et al. for the following features:
1) it contains one single nucleic acid probe, namely LCF, which is labeled at its 3'-end with fluorescein;
2) it does not include any loop primer LoopB, and the latter is replaced with the LCQ primer, which is labeled at its 5'-end with the fluorescent moiety LC640. In the light of the above, the method by Chou et al. provides for the generation of a fluorescent amplification signal by means of the FRET mechanism between a labeled donor probe and a labeled acceptor probe. Conversely, in the method according to the present invention the function of acceptor oligonucleotide is carried out by one of the loop primers, previously labeled, thereby reducing the number of oligonucleotides employed in the LAMP reaction. Moreover, the method of the invention overcomes the disadvantage associated with the assay by Chou et al. of a possible competition of the FRET probes employed in said assay with the loop primers for the binding to the same target nucleotide sequence.

In the present study, the following primer concentrations were used in the LAMP reactions: 0.375 μM outer primers (F3 and B3), 2 μM inner primers (FIP and BIP), 1.1 μM loop primer LoopF, 0.3 µM loop primer LoopB (present only in the reaction according to Chou et al), 0.25 µM LCF and LCQ.

The LAMP reactions were performed in a 20 µl mixture containing: 0.375 mM dNTPs, 2.4 U of Bst DNA polymerase Large Fragment (New England BioLabs, Beverly, Mass., USA), 1× Reaction Buffer (20 mM HEPES buffer, pH 7.9, 20 mM KCl, 3 mM MgCl2, and 0.1% Triton X100).

The reaction mixtures were incubated at 60° C. for 120 minutes on a Rotor-Gene Q instrument (Qiagen). The amplification products were then kept at 4° C.

LAMP amplification of the recombinant WSSV plasmid was detected by the analysis of the normalized fluorescent signal generated during the reaction. The Threshold time was identified by setting a fluorescence threshold at 0.2, corresponding at around 50% of the fluorescence increment.

Data Analysis and Normalization

Data analysis was performed using the statistical package within the Microsoft Excel. The same package was used for linear regression analysis.

Data normalization was obtained by means of the Rotor-Gene Pure Detection v2.1 Software.

Example 2

Comparison of the LAMP Method of the Invention with an Intercalating Dye-Based LAMP Assay Sample Preparation In order to compare the performance of the method of the invention with a LAMP assay that involves the use of intercalating dyes, a suitable target nucleic acid sequence was prepared. Briefly, a 350-bp DNA fragment derived from the MYH11 gene (GenBank D10667.1) was cloned into the pMA-T vector (GENEART) by using the Sfi I/Sfi I restriction site combination to provide the positive control.

The recombinant MYH11 plasmid was serially diluted 10-fold in buffer Tris-HCl 10 mM, pH 8.5, from approximately $2\times10^6$ copies/µL to $2\times10^1$ copies/µL.

In the present study, the analyzed plasmid dilutions were denatured at 100° C. for 10 minutes. After denaturation, the plasmid samples were immediately placed on ice for 10 minutes.

LAMP Reaction

In Table 2 below are listed the LAMP oligonucleotide primers and probes employed for the comparative analysis.

TABLE 2

| Oligo name | Sequence (5'->3') | SEQ ID NO: |
|---|---|---|
| F3 | TCAAGAAACTGGAGGATGAG (Forward outer primer) | 9 |
| B3 | TTCCGTTTCAGCTTCTCC (Reverse outer primer) | 10 |
| FIP | TGTCGTTAAGTCACTAATCCTCTGGTCATGGATGATCAGA (Forward inner primer) | 11 |
| BIP | GCCAAGAATCTTACCAAGCTGAAGGCTCTTCTCTTCC (Reverse inner primer) | 12 |
| Donor Probe | GAATCTATGATTTCAG-Bodipy FL (3' Bodipy FL-labeled FRET probe) | 13 |
| Acceptor LB loop | ATTO 647N-ACTGGAAGTGCGGCTAAAG (Reverse 5' ATTO647N labeled loop) | 14 |

In the LAMP reaction according to the method of the invention, the following oligonucleotide concentrations were used: 0.05 µM outer primers (F3 and B3), 0.4 µM inner primers (FIP and BIP), 0.2 µM Acceptor LB loop primer and 0.2 µM Donor FRET probe. Conversely, besides the above-indicated outer and inner primers, the oligonucleotides set employed in the intercalating dye-based LAMP assay included only the LB loop primer in non-labeled form.

The LAMP reactions were performed in a 25 µl mixture containing: 1.4 mM dNTPs, 8 U of Bst DNA polymerase Large Fragment (New England BioLabs, Beverly, Mass., USA), 8 mM MgCl2, 1× Reaction Buffer (30 mM Tris-HCl, pH 8.0, 30 mM KCl, and 0.1% Triton X100).

The reaction mixtures set up for the intercalating dye-based LAMP assay further included the YO-PRO intercalating dye (Life Technologies) at the concentration of 1 µM.

The LAMP amplification reaction was conducted at 65° C. for 40 minutes on a Rotor-Gene Q instrument (Qiagen). The amplification products were then kept at 4° C.

LAMP amplification of the recombinant MYH11 plasmid was detected by the analysis of the normalized fluorescent signal generated during the reaction. The Threshold time was identified by setting a fluorescence threshold at 0.2, corresponding at around 50% of the fluorescence increment.

Data Analysis and Normalization

Data analysis was performed using the statistical package within the Microsoft Excel. The same package was used for linear regression analysis.

Data normalization was obtained by means of the Rotor-Gene Pure Detection v2.1 Software.

Example 3

Comparison of the LAMP Method of the Invention with a Guanine Quenching-Based LAMP Assay Sample Preparation A performance assessment of the method of the present invention was performed in comparison with a LAMP assay involving the mechanism of fluorophore guanine quenching, for the detection of amplification signal. Briefly, a suitable target nucleic acid sequence was prepared by cloning a 240-bp DNA fragment derived from the GUS beta gene (GenBank: NM_000181.3) into the pMK-RQ (kanR) vector (Life Technologies). The cloning strategy made use of the Sfi I/Sfi I restriction site combination.

The recombinant GUS beta plasmid was serially diluted 10-fold in buffer Tris-HCl 10 mM, pH 8.5, from approximately $2\times10^6$ copies/µL to $2\times10^1$ copies/µL.

In the present study, the analyzed plasmid dilutions were denatured at 100° C. for 10 minutes. After denaturation, the plasmid samples were immediately placed on ice for 10 minutes.

LAMP Reaction

The oligonucleotide primers and probes employed in the LAMP reactions are illustrated in Table 3 below.

TABLE 3

| Oligo name | Sequence (5'->3') | SEQ ID NO: |
|---|---|---|
| F3 | TAGAGCATGAGGGGGGCTA (Forward outer primer) | 15 |
| B3 | GTGTTCTGGACAAAGTAACC (Reverse outer primer) | 16 |

TABLE 3-continued

| Oligo name | Sequence (5'->3') | SEQ ID NO: |
|---|---|---|
| FIP | GGCGATAGTGATTCGGAGCATCAGCAACCTGGT (Forward inner primer) | 17 |
| BIP | CAACAACACACTCACCCCTTGGGATACTTGGAGG (Reverse inner primer) | 18 |
| Acceptor Quencher Probe | CCACCCTGCCACCAGGG-BHQ3 (3'BHQ3-labeled Quencher FRET probe) | 19 |
| Donor LB loop | Bodipy630-CCATCCAATACCTGACT (Reverse 5'Bodipy630 labeled loop) | 20 |

In the LAMP method of the invention, the oligonucleotide primers and probes were used at the following concentrations: 0.03 µM outer primers (F3 and B3), 0.3 µM inner primers (FIP and BIP), 0.2 µM LB loop primer and 0.2 µM Quencher probe. According to the present invention, the LB loop primer is labeled at its 5'-end with a BODIPY 630 molecule, whereas the Quencher probe is labeled at its 3'-end with a Black Hole Quencher 3 molecule.

In order to perform the above detailed comparative analysis, the LAMP amplification experiments were conducted either in the presence or in the absence of the Quencher probe.

The LAMP reactions were performed in a 25 µL mixture containing: 1.2 mM dNTPs, 6 mM MgCl2, 8 U of Bst DNA polymerase Large Fragment (New England BioLabs, Beverly, Mass., USA), 1× Reaction Buffer (30 mM Tris-HCl, pH 8.0, 30 mM KCl, and 0.1% Triton X100).

LAMP amplification was performed at 63° C. for minutes on the AB7500 instrument (Life Technologies). The amplification products were then kept at 4° C.

The reaction mixture was incubated at 63° C. for 40 minutes using the AB7500 instrument (Life Technologies).

Data Analysis

Data analysis was performed by calculating the Fluorescence quenching signal using the raw data returned by the SDS software (v 2.3).

The Quenching rate was calculated as equal to 100−((Min/Max)*100).

Linear regression analysis was performed using the statistical package within the Microsoft Excel.

The invention claimed is:

1. A method of detecting loop-mediated isothermal amplification (LAMP) of a target nucleic acid sequence, the method comprising the steps of:
   i) contacting a test sample possibly containing the nucleic acid target sequence with DNA polymerase having strand displacement activity and a set of oligonucleotides LAMP primers consisting of:
   a. a first outer primer F3 and a second outer primer B3;
   b. a first inner primer FIP and a second inner primer BIP;
      wherein FIP consists of a 3' nucleic acid sequence F2 and a 5' nucleic acid sequence F1c and BIP consists of a 3' nucleic acid sequence B2 and a 5' nucleic acid sequence B1c;
      wherein F2 is complementary to a F2c region of the target nucleic acid sequence and B2 is complementary to a B2c region of the target nucleic acid sequence;
      wherein F2c and B2c are non-overlapping regions located on opposite strands of the target nucleic acid sequence;
   c. a first loop primer LF and optionally a second loop primer LB;
      wherein LF is capable of hybridizing to a region between F2 and F1, and LB is complementary to a region between B1 and B2; and
      wherein either the loop primer LF, or the loop primer LB, if present, is labeled with at least one acceptor fluorophore at its 5'-end; and
   d. one nucleic acid probe which is capable of hybridizing to the target nucleic acid sequence at a position which is 5' to the labeled LF or LB loop primer, so that, when the nucleic acid probe is hybridized to the target nucleic acid sequence, the 3'-end of the nucleic acid probe is brought into close proximity to the 5'-end of the labeled LF or LB loop primer;
      wherein the nucleic acid probe is labeled at its 3'-end with at least one donor fluorophore capable of transferring excitation energy to the at least one acceptor fluorophore of the LF or LB loop primer, and
      wherein the intensity of fluorescence emission of the acceptor fluorophore increases upon absorption of the donor fluorophore excitation energy; and
   ii) detecting a change in a fluorescence parameter that is generated upon incorporation of the labeled loop-primer in the LAMP amplification product as an indication of LAMP amplification of the target nucleic acid sequence, wherein the change in the fluorescence parameter is an increase in the intensity of the fluorescence emission of the acceptor fluorophore.

2. The method according to claim 1, wherein the 3'-end of the nucleic acid probe, when hybridized to the target nucleic acid sequence, is spaced from the 5'-end of the labeled LF or LB loop primer by not more than 6 nucleotides.

3. The method according to claim 1, wherein the labeled LF or LB loop primer is a stem-loop extensible primer comprising:

i) a central loop sequence able to selectively recognize and hybridize to the respective region of the target nucleic acid sequence, and
   ii) a 5' end sequence and a 3' end sequence which are complementary to each other such as to form a double-stranded stem.

4. The method according to claim 2, wherein the labeled LF or LB loop primer is a stem-loop extensible primer comprising:
   i) a central loop sequence able to selectively recognize and hybridize to the respective region of the target nucleic acid sequence, and
   ii) a 5' end sequence and a 3' end sequence which are complementary to each other such as to form a double-stranded stem.

5. The method according to claim 1, wherein the target nucleic acid sequence comprises at least one mutation, which is a point mutation, a deletion, an insertion, or a translocation.

6. The method according to claim 2, wherein the target nucleic acid sequence comprises at least one mutation, which is a point mutation, a deletion, an insertion, or a translocation.

7. The method according to claim 3, wherein the target nucleic acid sequence comprises at least one mutation, which is a point mutation, a deletion, an insertion, or a translocation.

8. The method according to claim 5, wherein amplification of the target nucleic acid sequence is indicative of the presence or of the absence of the at least one mutation.

9. The method according to claim 6, wherein amplification of the target nucleic acid sequence is indicative of the presence or of the absence of the at least one mutation.

10. The method according to claim 7, wherein amplification of the target nucleic acid sequence is indicative of the presence or of the absence of the at least one mutation.

11. The method according to claim 1, wherein the 3'-end of the nucleic acid probe, when hybridized to the target nucleic acid sequence, is spaced from the 5'-end of the labeled LF or LB loop primer by not more than 1 nucleotide.

12. The method according to claim 1, wherein the 3'-end of the nucleic acid probe, when hybridized to the target nucleic acid sequence, is immediately adjacent to the 5'-end of the labeled LF or LB loop primer.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: artificial sequence
<220> FEATURE:
<223> OTHER INFORMATION: Forward outer primer

<400> SEQUENCE: 1
tgattcagat ggcatggata ctt                                                23

<210> SEQ ID NO 2
<211> LENGTH: 20
<212> TYPE: DNA
<213> ORGANISM: artificial sequence
<220> FEATURE:
<223> OTHER INFORMATION: Reverse outer primer

<400> SEQUENCE: 2
ccgatactgc cattgaaagc                                                    20

<210> SEQ ID NO 3
<211> LENGTH: 49
<212> TYPE: DNA
<213> ORGANISM: artificial sequence
<220> FEATURE:
<223> OTHER INFORMATION: Forward inner primer

<400> SEQUENCE: 3
tgttatggta gtgaacccct ttgcacgact tatcattcaa gacatcaat                    49

<210> SEQ ID NO 4
<211> LENGTH: 49
<212> TYPE: DNA
<213> ORGANISM: artificial sequence
<220> FEATURE:
<223> OTHER INFORMATION: Reverse inner primer

<400> SEQUENCE: 4
ggaagaaaga tacaagccca ttggcgctcc cttaccacct tccttaatc                49

<210> SEQ ID NO 5
<211> LENGTH: 22
<212> TYPE: DNA
<213> ORGANISM: artificial sequence
<220> FEATURE:
<223> OTHER INFORMATION: Reverse loop primer

<400> SEQUENCE: 5
gccattgaag cagtgttggg at                                             22

<210> SEQ ID NO 6
<211> LENGTH: 25
<212> TYPE: DNA
<213> ORGANISM: artificial sequence
<220> FEATURE:
<223> OTHER INFORMATION: Forward loop primer

<400> SEQUENCE: 6
gatcgttaac aacaacaata ctgga                                          25

<210> SEQ ID NO 7
<211> LENGTH: 19
<212> TYPE: DNA
<213> ORGANISM: artificial sequence
<220> FEATURE:
<223> OTHER INFORMATION: 3' fluoresceine labeled FRET probe

<400> SEQUENCE: 7
cacccacagc ggctcttgc                                                 19

<210> SEQ ID NO 8
<211> LENGTH: 24
<212> TYPE: DNA
<213> ORGANISM: artificial sequence
<220> FEATURE:
<223> OTHER INFORMATION: 5' LC640 labeled FRET probe

<400> SEQUENCE: 8
cgttcgccat tgaagcagtg ttgg                                           24

<210> SEQ ID NO 9
<211> LENGTH: 20
<212> TYPE: DNA
<213> ORGANISM: artificial sequence
<220> FEATURE:
<223> OTHER INFORMATION: Forward outer primer

<400> SEQUENCE: 9
tcaagaaact ggaggatgag                                                20

<210> SEQ ID NO 10
<211> LENGTH: 18
<212> TYPE: DNA
<213> ORGANISM: artificial sequence
<220> FEATURE:
<223> OTHER INFORMATION: Reverse outer primer

<400> SEQUENCE: 10
ttccgtttca gcttctcc                                                  18

<210> SEQ ID NO 11
<211> LENGTH: 40
<212> TYPE: DNA
<213> ORGANISM: artificial sequence

```
<220> FEATURE:
<223> OTHER INFORMATION: Forward inner primer

<400> SEQUENCE: 11
tgtcgttaag tcactaatcc tctggtcatg gatgatcaga                                40

<210> SEQ ID NO 12
<211> LENGTH: 37
<212> TYPE: DNA
<213> ORGANISM: artificial sequence
<220> FEATURE:
<223> OTHER INFORMATION: Reverse inner primer

<400> SEQUENCE: 12
gccaagaatc ttaccaagct gaaggctctt ctcttcc                                   37

<210> SEQ ID NO 13
<211> LENGTH: 16
<212> TYPE: DNA
<213> ORGANISM: artificial sequence
<220> FEATURE:
<223> OTHER INFORMATION: 3' Bodipy FL-labeled FRET probe

<400> SEQUENCE: 13
gaatctatga tttcag                                                          16

<210> SEQ ID NO 14
<211> LENGTH: 19
<212> TYPE: DNA
<213> ORGANISM: artificial sequence
<220> FEATURE:
<223> OTHER INFORMATION: Reverse 5' ATTO647N labeled loop

<400> SEQUENCE: 14
actggaagtg cggctaaag                                                       19
```